United States Patent
Foley (10) Patent No.: US 9,437,333 B2
(45) Date of Patent: Sep. 6, 2016

(54) APPARATUS AND METHOD TO CONTROL SENSOR POSITION IN LIMITED ACCESS AREAS WITHIN A NUCLEAR REACTOR

(71) Applicant: WESTINGHOUSE ELECTRIC COMPANY LLC, Cranberry Township, PA (US)

(72) Inventor: Kevin J. Foley, Chattanooga, TN (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 683 days.

(21) Appl. No.: 13/802,907

(22) Filed: Mar. 14, 2013

(65) Prior Publication Data

US 2014/0098924 A1    Apr. 10, 2014

Related U.S. Application Data

(60) Provisional application No. 61/711,239, filed on Oct. 9, 2012.

(51) Int. Cl.
*G21C 19/20* (2006.01)
*G21C 17/003* (2006.01)
(Continued)

(52) U.S. Cl.
CPC .............. *G21C 19/20* (2013.01); *G01N 29/225* (2013.01); *G01N 29/265* (2013.01); *G21C 17/003* (2013.01); *G21C 17/013* (2013.01); *G21C 19/207* (2013.01)

(58) Field of Classification Search
CPC ... G21C 19/20; G21C 17/003; G21C 17/013
USPC ........................................ 376/245, 249, 260
See application file for complete search history.

(56) References Cited

U.S. PATENT DOCUMENTS 4,213,732 A * 7/1980 Cooper ......................... 376/260
5,215,706 A * 6/1993 Cross et al. ................... 376/245
(Continued)

FOREIGN PATENT DOCUMENTS

JP      H07110320 A    4/1995
JP      2619020 B2     6/1997
(Continued)

OTHER PUBLICATIONS

International Search Report and Written Opinion of the International Searching Authority for PCT/US2013/063633 dated Jul. 10, 2014 (Forms PCT/ISA/220, PCT/ISA/210, PCT/ISA/237).
(Continued)

*Primary Examiner* — Jack W Keith
*Assistant Examiner* — Daniel Wasil
(74) *Attorney, Agent, or Firm* — Joseph C. Spadacene; Westinghouse Electric Company LLC (57) ABSTRACT

This invention concerns robotic systems and is specifically concerned with an improved apparatus and method for remotely positioning a sensor, such as an ultrasonic probe, in limited access areas within a nuclear reactor. The apparatus includes a bottom frame and a top cover which is substantially aligned with and positioned above the bottom frame. A sensor is connected to the top cover and linear rails are connected to the bottom frame in a parallel relationship. There is a mechanism movably connected to the first and second linear rails in order to allow horizontal travel of the top cover. Further, there is at least one cable connected to the sensor and a power source, signal source or receiver.

7 Claims, 12 Drawing Sheets

(51) Int. Cl.
  *G21C 17/013* (2006.01)
  *G01N 29/22* (2006.01)
  *G01N 29/265* (2006.01)

(56) References Cited

U.S. PATENT DOCUMENTS

| | | | |
|---|---|---|---|
| 5,444,746 A * | 8/1995 | Okamoto et al. | 376/245 |
| 5,544,206 A * | 8/1996 | Brooks et al. | 376/245 |
| 5,784,425 A | 7/1998 | Morlan | |
| 5,955,852 A * | 9/1999 | Jentsch | 318/282 |
| 6,058,153 A * | 5/2000 | Kurosawa et al. | 376/260 |
| 6,145,583 A * | 11/2000 | Gay et al. | 376/245 |
| 7,308,069 B2 * | 12/2007 | Legard et al. | 376/245 |
| 8,046,959 B2 * | 11/2011 | Stoetzer et al. | 52/116 |
| 9,117,554 B2 * | 8/2015 | Vigliano | G21C 17/003 376/249 |
| 2007/0146480 A1 | 6/2007 | Judge, Jr. et al. | |

FOREIGN PATENT DOCUMENTS

| | | |
|---|---|---|
| JP | H09211182 A | 8/1997 |
| JP | 2006061976 A | 3/2006 |

OTHER PUBLICATIONS

International Preliminary Report on patentability for PCT/US2013/063633 dated Apr. 23, 2015 (Forms PCT/IB/326, PCT/IB/373, PCT/ISA/237).

* cited by examiner

APPARATUS AND METHOD TO CONTROL SENSOR POSITION IN LIMITED ACCESS AREAS WITHIN A NUCLEAR REACTOR

CROSS-REFERENCE TO RELATED APPLICATIONS

This application claims priority under 35 U.S.C. Section 119(e) from Provisional Application 61/711,239, entitled "Apparatus and Method to Control Sensor Position in Limited Access Areas Within a Nuclear Reactor" filed on Oct. 9, 2012.

FIELD OF THE INVENTION

This invention generally concerns robotic systems and is specifically concerned with an improved apparatus and method for remotely positioning a sensor, such as an ultrasonic probe, in limited access areas within a nuclear reactor.

BACKGROUND OF THE INVENTION

A nuclear reactor produces electrical power by heating water in a reactor pressure vessel that contains a nuclear fuel core in order to generate steam which is used in turn to drive a steam turbine. Various components and structures in a nuclear reactor are examined periodically assess its structural integrity and determine the need for repair. Ultrasonic inspection is a known technique for detecting cracks in nuclear reactor components. The inspection areas in the nuclear reactor may have limited access and therefore, difficult to assess using an inspection tool. For example, the core shroud welds are periodically assessed for stress corrosion cracking. The presence of stress corrosion cracking can diminish the structural integrity of the core shroud. However, the core shroud is difficult to access. Installation access is limited to the annular space between the outside of the shroud and the inside of the reactor pressure vessel, between adjacent jet pumps. Scanning operation access is additionally restricted within the narrow space between the shroud and jet pumps.

Further, the inspection areas in a nuclear reactor can be highly radioactive and can pose safety risks for personnel working in these areas. Thus, inspection of these areas for the most part can require a robotic device which can be installed remotely and operated within the narrowly restricted space.

Inspecting and repairing nuclear reactors, such as boiling water reactors, typically consist of manually controlled poles and ropes to manipulate servicing devices and/or positioning of these devices. During reactor shut down, servicing of some components require installation of inspection manipulators or devices 30 to 100 feet deep within reactor coolant. Relatively long durations are required to install or remove manipulators and can impact the plant shutdown duration. In addition, different inspection scopes can require several manipulator reconfigurations requiring additional manipulator installations and removals. The long durations cannot only impact plant shutdown durations, but also increase personnel radiation and contamination exposure.

Plant utilities have a desire to reduce the number of manipulator installations and removals to reduce radiological exposure as well as cost and plant outage impact. This invention allows the number of reconfigurations, installations and removals to be minimized. It is contemplated that if utilized on currently available manipulators, approximately one-half of the configurations may be eliminated.

SUMMARY OF THE INVENTION

The invention provides apparatus and methods for inspecting a core shroud in a reactor vessel. In one aspect, the invention provides an apparatus for remotely positioning a sensor in an area of a nuclear reactor. The apparatus includes a bottom frame, a top cover having a first end and a second end, the top cover substantially aligned with the bottom frame and positioned above the bottom frame, a sensor connected to the first end of the top cover, a first linear rail, a second linear rail substantially aligned in a parallel relationship to the first linear rail, a mechanism movably connected to each of the first and second linear rails and connected to the top cover, wherein the mechanism is effective to horizontally move the top cover relative to the bottom frame, and at least one cable having a first end and a second end, the first end being connected to the sensor and a second end being connected to a power source, signal source or receiver.

The apparatus can further include a protective cover connected to the bottom frame and effective to house a portion of the cable. The apparatus can also further include a two bar linkage system including a first bar having a first end and a second end, a second bar having a first end and a second end, the first end of the first bar connected to a pin which is attached to the bottom frame, the second end of the first bar connected to a pivot pin, the first end of the second bar connected to a pin which is attached to the top cover, and the second end of the second bar connected to the pivot pin, wherein when the top cover is moved horizontally the two bar linkage system is in an extended position.

In the apparatus, the first end of the top cover can have an access hole positioned therein to interface with a manual pick device to extend or retract the apparatus. The apparatus can further include at least two hydraulic cylinders at least partially attached to the top cover to horizontally drive the top cover from a first position to a second position to extend the sensor from a first position to a second position.

The cable can extend from the sensor through the two bar linkage system such that the linkage system protects the cable.

The first end of the top cover can be connected to an arm of an inspection tool and the sensor can be effective to inspect a component in a nuclear reactor. In certain embodiments, the component is a core shroud in a reactor pressure vessel. The tool can be positioned on the core shroud and the apparatus can be positioned in an annulus formed between the core shroud and a wall of the reactor pressure vessel.

In another aspect, the invention provides a method for remotely positioning a sensor in an area of a nuclear reactor. The method includes obtaining a sensor positioning apparatus including a bottom frame, a top cover having a first end and a second end, the top cover substantially aligned with the bottom frame and positioned above the bottom frame, a sensor connected to the first end of the top cover, a first linear rail, a second linear rail substantially aligned in a parallel relationship to the first linear rail, a mechanism movably connected to each of the first and second linear rails and connected to the top cover, wherein the mechanism is effective to horizontally move the top cover relative to the bottom frame, and at least one cable having a first end and a second end, the first end being connected to the sensor and a second end being connected to a power source, signal source or receiver, and connecting the sensor positioning apparatus to an inspection tool.

In another aspect, the apparatus of the invention is used to position a sensor attached thereto to a specific location relative to a sensor that is attached to an inspection tool.

BRIEF DESCRIPTION OF THE DRAWINGS

A further understanding of the invention can be gained from the following description of the preferred embodiments when read in conjunction with the accompanying drawings in which:

FIGS. 10A and 10B are top views of the sensor positioning apparatus of FIG. 9 with the top cover removed; FIG. 10A shows the sensor and two bar linkage in an extended configuration, in accordance with certain embodiments of the invention; and FIG. 10B shows the sensor and two bar linkage in a contracted configuration, in accordance with certain embodiments of the invention.

DETAILED DESCRIPTION OF THE PREFERRED EMBODIMENTS

It will be understood that, although the terms first, second, etc. may be used herein to describe various elements, these elements should not be limited by these terms. There terms are only used to distinguish one element from another. For example, a first element could be termed a second element, and similarly, a second element could be termed a first element, without departing from the scope of the embodiments. As used herein, the term "and/or" includes any and all combinations of one or more of the associated listed items.

It should be understood that when an element of component is referred to as being "on", "connected to," "coupled to," or "covering" another element or layer, it may be directly on, connected to, coupled to, or covering the other element or layer or intervening elements or components may be present.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the present or addition of one or more other features, integers, steps, operations, elements, components and/or groups thereof.

The invention relates to robotic devices for remotely positioning a sensor, such as an ultrasonic probe, in limited access areas within a nuclear reactor. The sensor can be employed to inspect or repair components and structures in the nuclear reactor which have limited access for the introduction and installation of an inspection or repair tool. In certain embodiments, these sensors are suitable for use in inspecting the core shroud of a nuclear reactor wherein the sensor is positioned in the narrow annulus formed between the core shroud and the wall of the reactor pressure vessel.

The invention can be used in light water nuclear reactors, such as boiling water reactors and pressurized water reactors.

The apparatus in accordance with certain embodiments of the invention generally is connected to a tool employed to inspect components and structures in a nuclear reactor and particularly those having limited access. In certain embodiments, the apparatus of the invention is connected to a tool for inspecting a core shroud in a reactor pressure vessel of a nuclear reactor. Typically, this inspection is conducted by positioning an inspection tool on the core shroud. The inspection tool includes an arm which extends vertically along the core shroud in an annulus space formed between the core shroud and the wall of the reactor pressure vessel. The arm and a sensor connected thereto are operable to move vertically and circumferentially along the core shroud to inspect the surface and welds contained therein. In certain embodiments, the apparatus of this invention is connected to a lower end of the arm to extend the vertical distance of the sensor along the core shroud. Further, the apparatus of the invention provides a means of protecting the cable through which power and signals are provided to the sensor. Moreover, the apparatus of the invention is operable hydraulically or pneumatically without the need for providing electrical wires.

The use of the apparatus of the invention will be described with regard to the inspection of a core shroud using a particular inspection tool. However, it is to be understood that the apparatus of the invention can be applied to inspecting, modifying and repairing procedures performed on a wide variety of components and structures in a nuclear reactor and the apparatus of the invention can be connected to various inspection tools that may be used to perform the inspections, modifications and repairs.

Figure 1A:
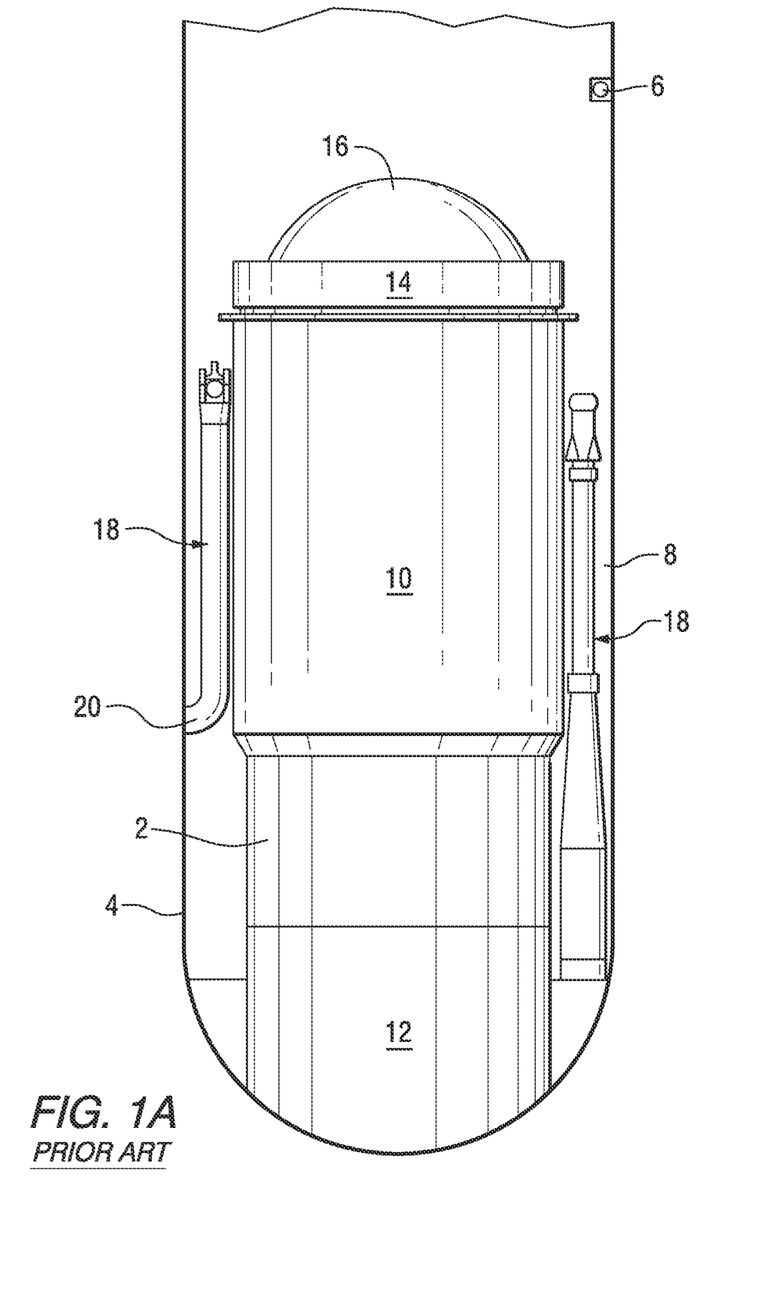
FIG. 1A is a schematic showing an elevational view of pertinent portions of a conventional BWR.

Referring to FIG. 1A, there is illustrated a core shroud 2 in a reactor pressure vessel (RPV) 4 of a conventional boiling water reactor (BWR). Feedwater is admitted into the RPV 4 via a feedwater inlet (not shown) and a feedwater sparger 6, which is a ring-shaped pipe having suitable apertures for circumferentially distributing the feedwater inside the RPV 4. The feedwater from the sparger 6 flows downwardly through a downcomer annulus 8, which is an annular region formed between the core shroud 2 and the RPV 4.

The core shroud 2 is a stainless steel cylinder surrounding the nuclear fuel core, the location of which is generally designated by numeral 10 in FIG. 1. The core is made up of a plurality of fuel bundle assemblies (not shown). Each array of fuel bundle assemblies is supported at the top by a top guide and at the bottom by a core plate (neither of which are shown). The core top guide provides lateral support for the top of the fuel assemblies and maintains the correct fuel channel spacing to permit control rod insertion.

The feedwater flows through the downcomer annulus 8, into jet pumps 18, and into the core lower plenum 12. The feedwater subsequently enters the fuel assemblies, wherein a boiling boundary layer is established. A mixture of water and steam enters a core upper plenum 14 under a shroud head 16. The steam-water mixture than flows through vertical standpipes (not shown) atop the shroud head 16 and enters steam separators (not shown), which separate liquid water from steam. The liquid water then mixes with feedwater in the mixing plenum, which mixture then returns to the reactor core via the downcomer annulus 8. The steam is withdrawn from the RPV via a steam outlet.

The BWR also includes a coolant recirculation system which provides the forced convection flow through the core which is necessary to attain the required power density. A portion of the water is removed from the lower end of the downcomer annulus 8 via a recirculation water outlet (not visible in FIG. 1) and forced by a centrifugal recirculation pump (not shown) into jet pump assemblies 18 (two of which are shown in FIG. 1A) via recirculation water inlets 20. The BWR has two recirculation pumps, each of which provides the driving flow for a plurality of jet pump assemblies. The jet pump assemblies are circumferentially distributed around the core shroud 2.

Figure 1B:
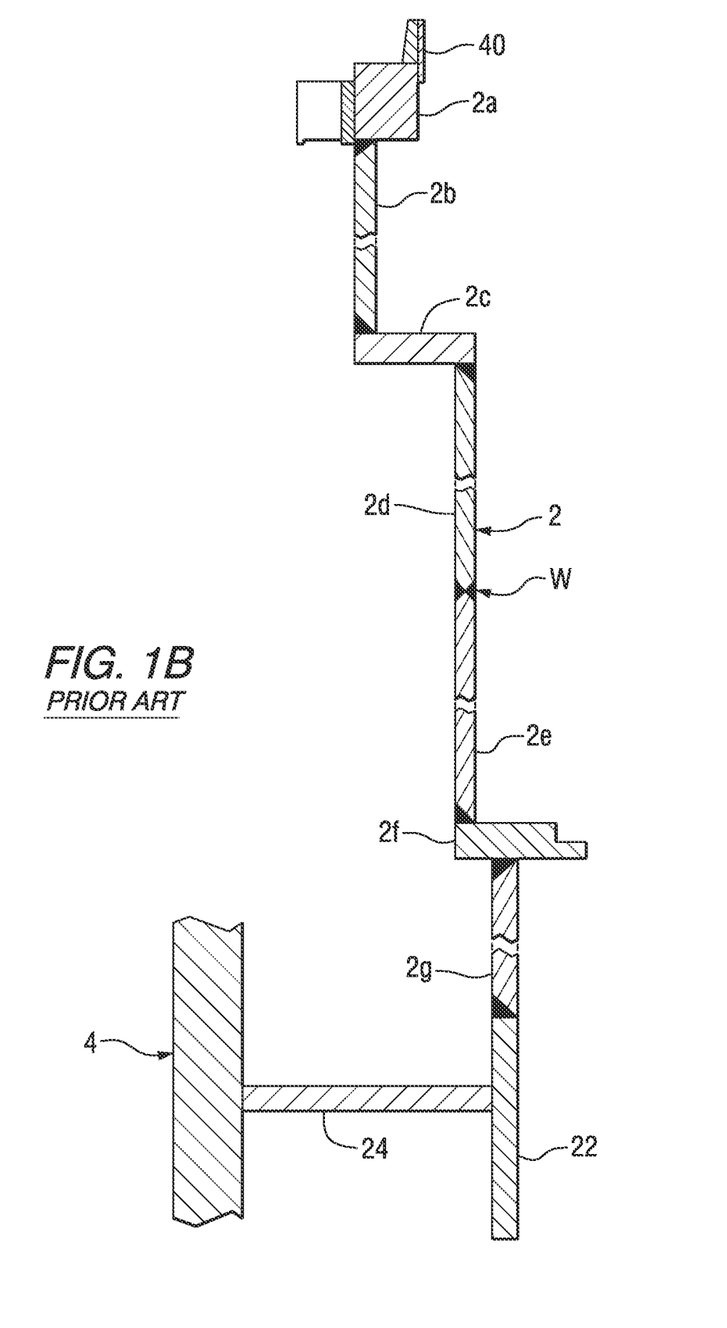
FIG. 1B is a sectional view of a portion of the core shroud incorporated in the BWR depicted in FIG. 1A.

Referring to FIG. 1B, there is illustrated the core shroud 2 in detail. There is a shroud head flange 2a for supporting the shroud head 16, a circular cylindrical upper shroud wall 2b having a top end welded to shroud head flange 2a, an annular top guide support ring 2c welded to the bottom end of the upper shroud wall 2b, a circular cylindrical middle shroud wall having a top end welded to top guide support ring 2c and consisting of upper and lower shell sections 2d and 2e joined by mid-shroud attachment weld, and an annular core plate support ring 2f welded to the bottom end of the middle shroud wall and to the top end of a lower shroud wall 2g. The entire shroud is supported by a shroud support 22, which is welded to the bottom of lower shroud wall 2g, and by annular jet pump support plate 24, which is welded at its inner diameter to shroud support 22 and at its outer diameter to RPV 4.

The material of the shroud and associated welds is austenitic stainless steel having reduced carbon content. The heat-affected zones of the shroud girth welds, including the mid-shroud attachment weld, have residual weld stresses. Therefore, the mechanisms are present for mid-shroud attachment weld W and other girth welds to be susceptible to stress corrosion cracking.

An inspection tool is in contact with the core shroud and remotely operated in the annulus formed between the reactor pressure vessel and the core shroud to perform an inspection of the core shroud and any welds associated therewith. The tool includes an upper partial track which is positioned, e.g., placed on or connected to, a portion of the core shroud, such as an upper annular rim of the core shroud. In one embodiment, the upper partial track is placed on the steam dam of the core shroud and is supported thereon by its center of gravity. The upper partial track guides a precision head and rigid frame structure which is movably coupled to the upper partial track. The rigid frame structure extends vertically downward from the precision head. The precision head and frame structure includes an electric motor and ball bearings or the like which allows the structure to travel horizontally along the upper partial track. Further, the upper track contains motors and brakes which are systemically configured to allow the use of this apparatus without a complete track ring. The head and frame structure houses a sensor positioner for performing inspections or repairs on upper barrel regions of the core shroud. The precision head and frame are also operable to position a moveable lower track. The lower track region houses a lower arm and positioner to perform inspections or repairs on middle and lower reactor core shroud barrel regions. The positioner is a two-axis positioner which allows displacement of the arm vertically and circumferentially along the core shroud. At least one sensor, such as an ultrasonic transducer, is connected to the lower arm for inspecting the core shroud. In certain embodiments, the lower arm can include multiple sensors in a spaced apart relationship to each other.

Figure 2:
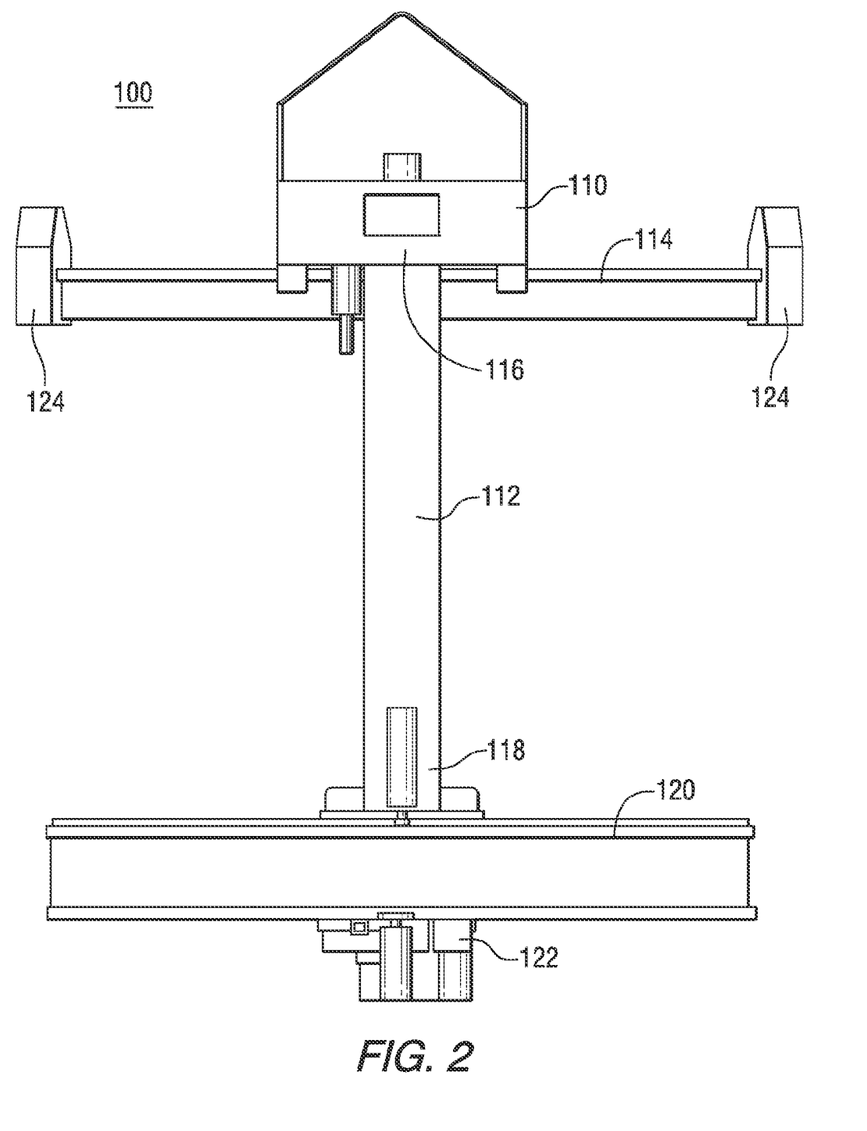
FIG. 2 is a front view of a core shroud inspecting apparatus, in accordance with certain embodiments of the invention.

Referring to FIG. 2, there is illustrated a core shroud inspecting tool generally referred to by reference character 100 for inspecting a core shroud in a nuclear reactor, in accordance with certain embodiments of the invention. The apparatus 100 includes a head 110, a frame 112 and a partial upper track 114. The frame 112 has an upper end 116 and an opposite lower end 118. The upper end 116 of the frame 112 is mounted to the head 110. The head 110 is connected to the partial upper track 114 for suitably moving in a horizontal direction relative to the partial upper track 114. The lower end 118 of the frame 112 is mounted to a lower track 120 for suitably moving the lower track 120 relative to the frame 112. A carriage 122 is coupled to the lower track 120 for suitably moving horizontally relative to the lower track 120. In certain embodiments, the partial upper track 114 and the lower track 120 are curved to suitably conform to the cylindrical shape of the core shroud in the nuclear reactor.

The partial upper track 114 includes a track brake system 124. When the track brake system 124 is activated, the partial upper track 114 remains stationary and the head 110 (and frame 112 mounted thereto) is horizontally movable along the partial upper track 114. When the track brake system 124 is deactivated or released, the partial upper track 114 can be driven into a different position along the rim of the core shroud. The track brake system 124 allows the head 110 and frame 112 to walk along the shroud without requiring a complete guide track ring. Thus, the head 110 and frame 112 are horizontally movable to drive along the partial upper track 114, or alternatively, the partial upper track 114 is horizontally movable to be driven into a different position along the rim of the core shroud.

Figure 3:
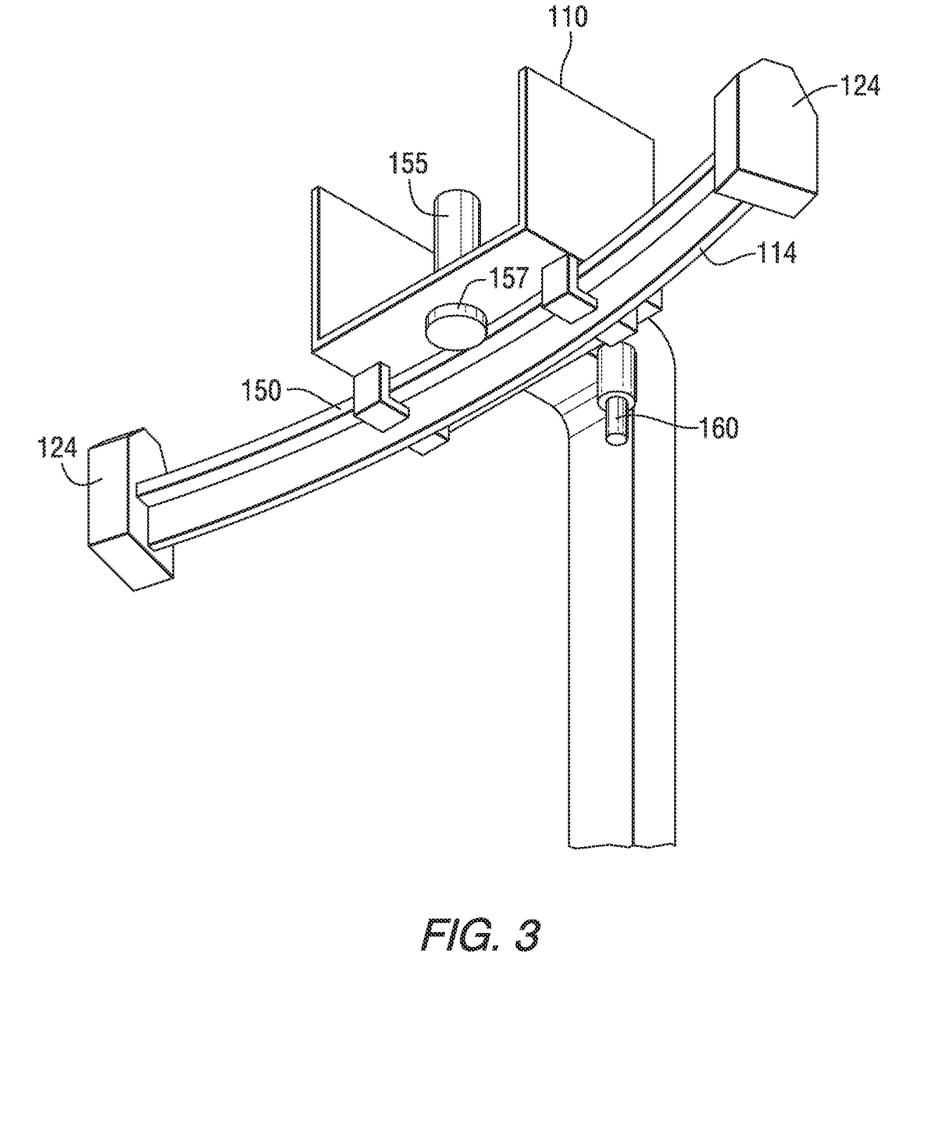
FIG. 3 is a perspective view of the core shroud inspecting apparatus of FIG. 2 showing a fixed gear rack mechanism, in accordance with certain embodiments of the invention.

Referring to FIG. 3, there is illustrated a fixed gear rack mechanism 150 for moving the partial upper track 114 along the core shroud. The fixed gear rack mechanism 150 interfaces with a positioning motor 155 and gear combination 157 located within the head 110. When the motor 155 is driven, the head 110 is moved relative to the partial upper track 114. If the track brake system 124 is applied, the partial upper track 114 will remain stationary relative to the core shroud and the head 110 moves relative to the partial upper track 114 and the core shroud. Alternatively, a positioning pin 160 can be pneumatically or hydraulically extended from the head 110 to react with reactor hardware positioned on the rim of the core shroud. If the position pin 160 is extended and the track brake system 124 is released, the head 110 remains stationary relative to the core shroud and the partial upper track will move relative to the core shroud. This provides for relocation of the entire apparatus 100 relative to the core shroud. The head motor 155 provides full position feedback so that global positioning of the entire apparatus is maintained and monitored within a tight tolerance.

Figure 4:
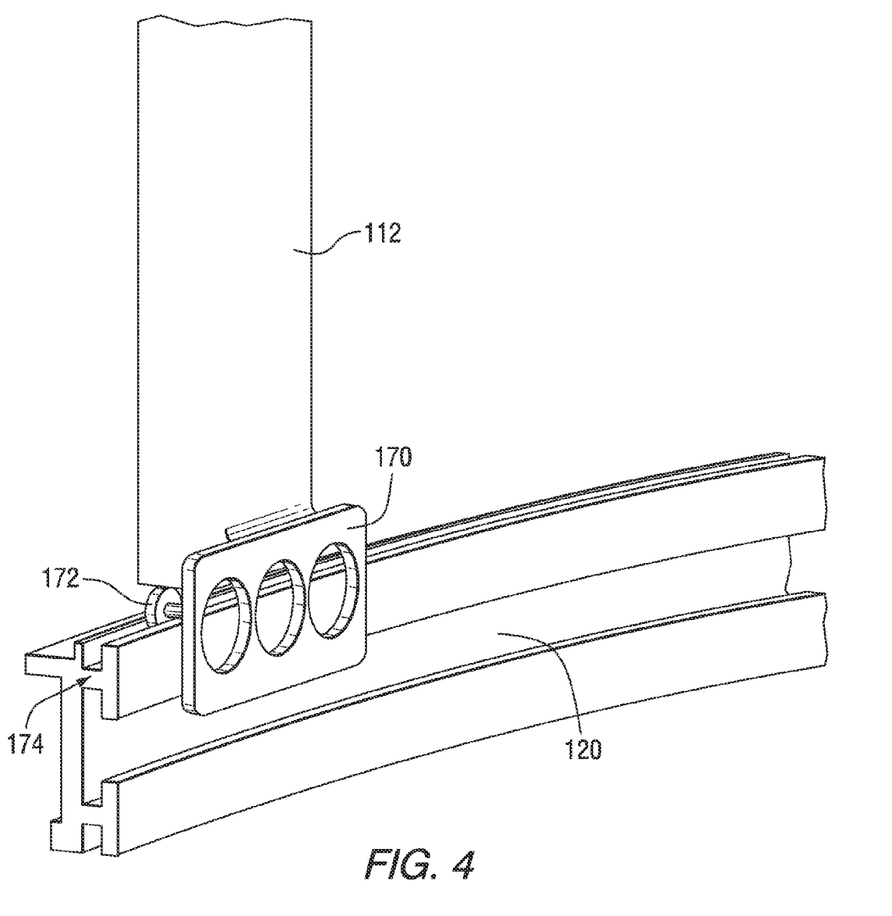
FIG. 4 is a perspective view of the core shroud inspecting apparatus of FIG. 2 showing a movable bearing system, in accordance with certain embodiments of the invention.

Referring to FIG. 4, there is illustrated a movable bearing system 170 which allows the lower track 120 to be driven relative to the frame 112 and to reach positions along the core shroud which are outside of the typical boundaries and obstructions exhibited by known apparatus. The frame 112 contains bearing wheels 172 that roll along guides 174 coupled to the lower track 120.

Figure 5:
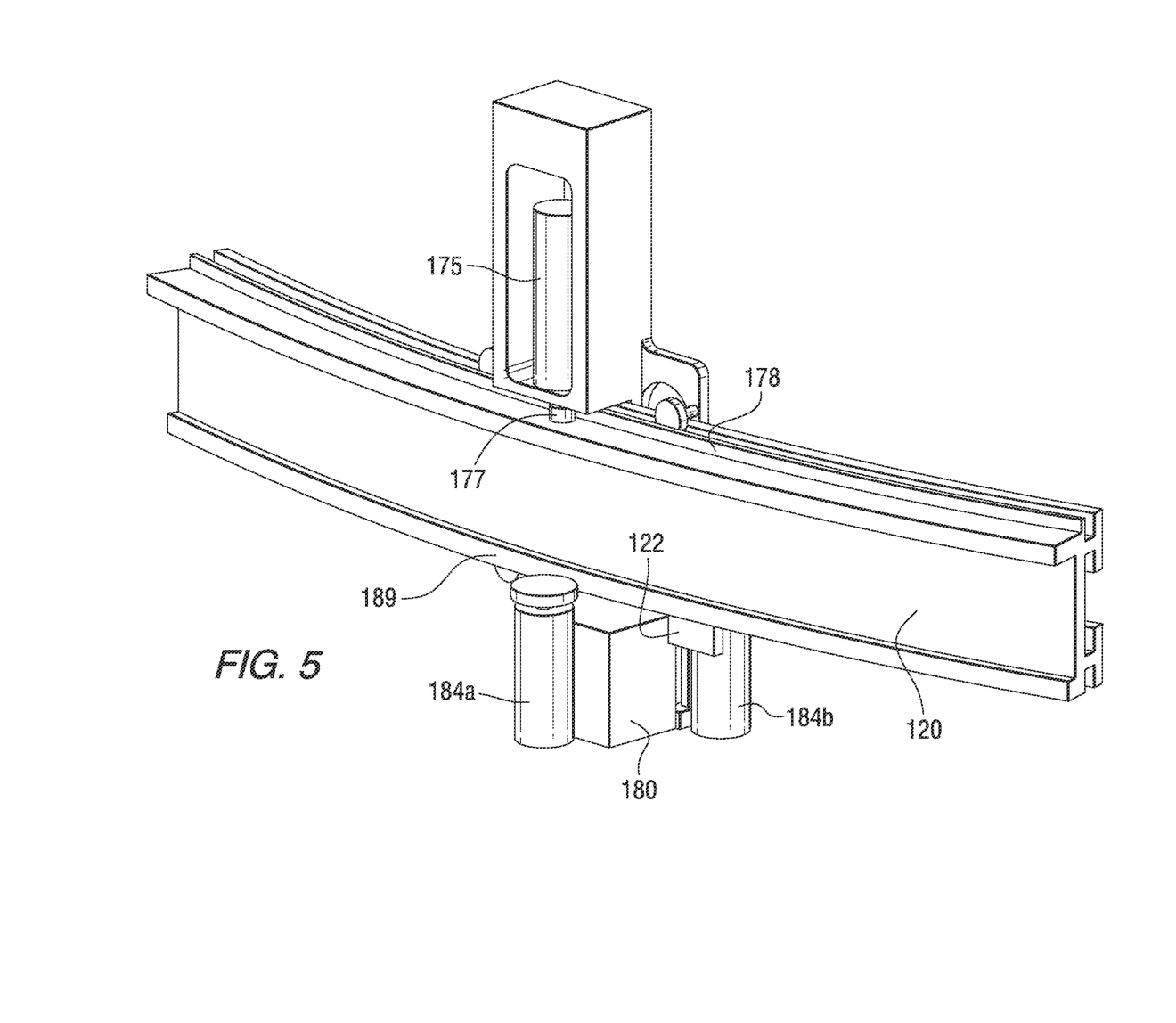
FIG. 5 is a detailed view of the lower track of the core shroud inspecting apparatus of FIG. 2, in accordance with certain embodiments of the invention.
Figure 6A:
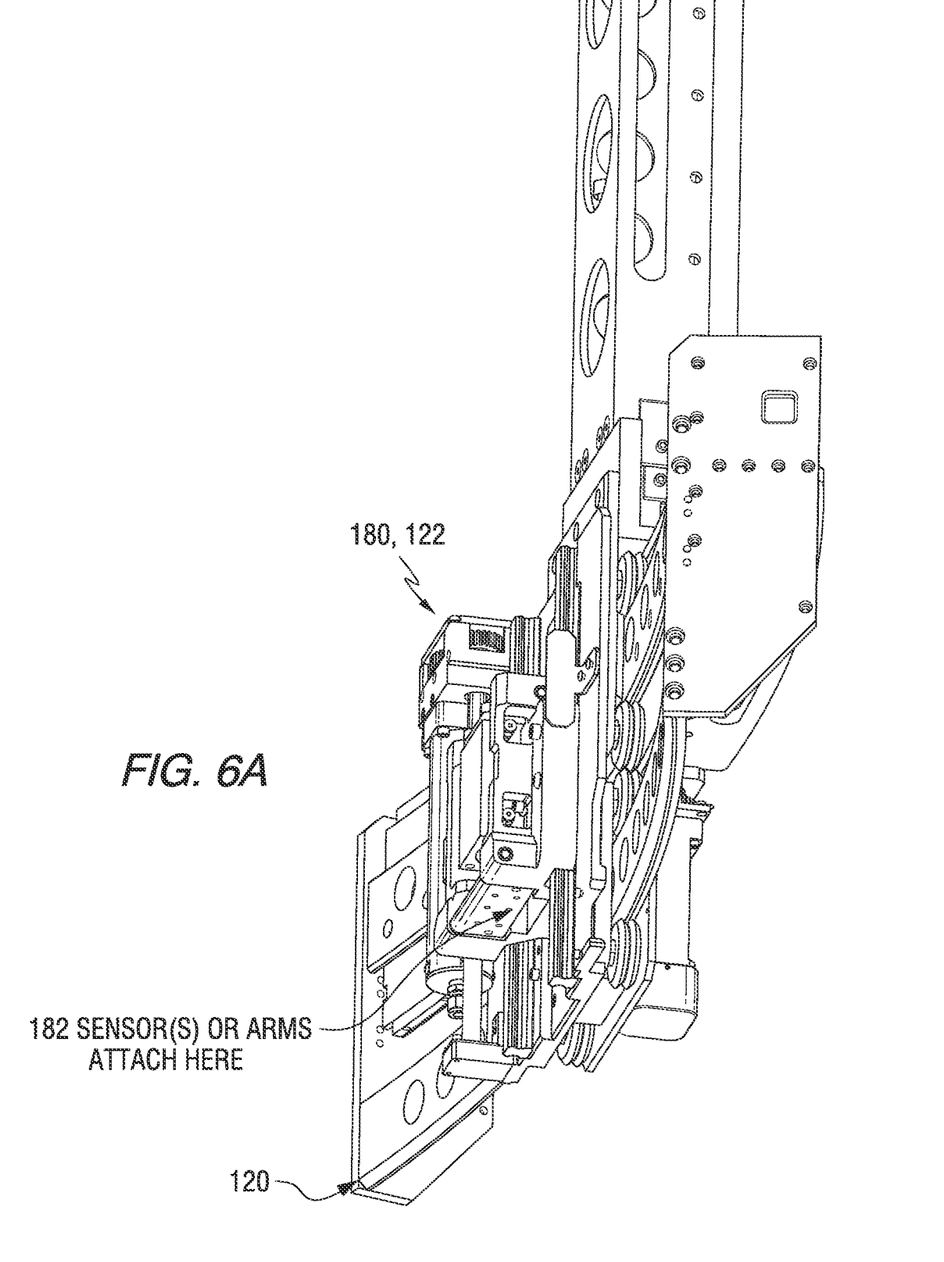
FIGS. 6A through 6D are detailed views of the precision positioners for the end effectors of the core shroud inspecting apparatus of FIG. 2, in accordance with certain embodiments of the invention.
Figure 6B:
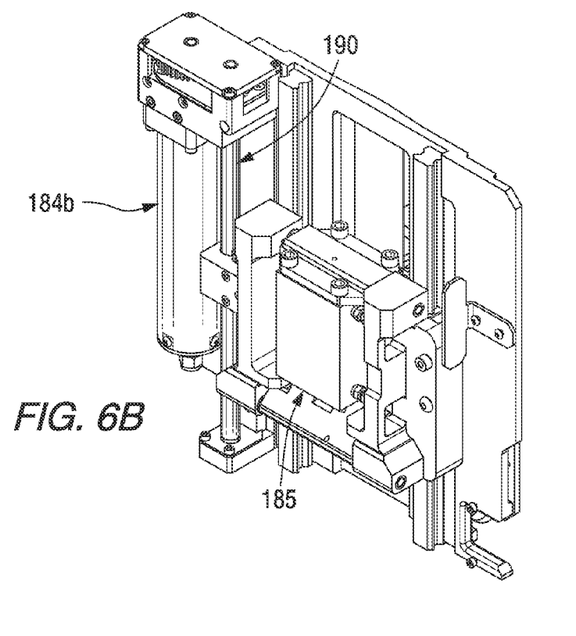
Figures 6C, 6D:
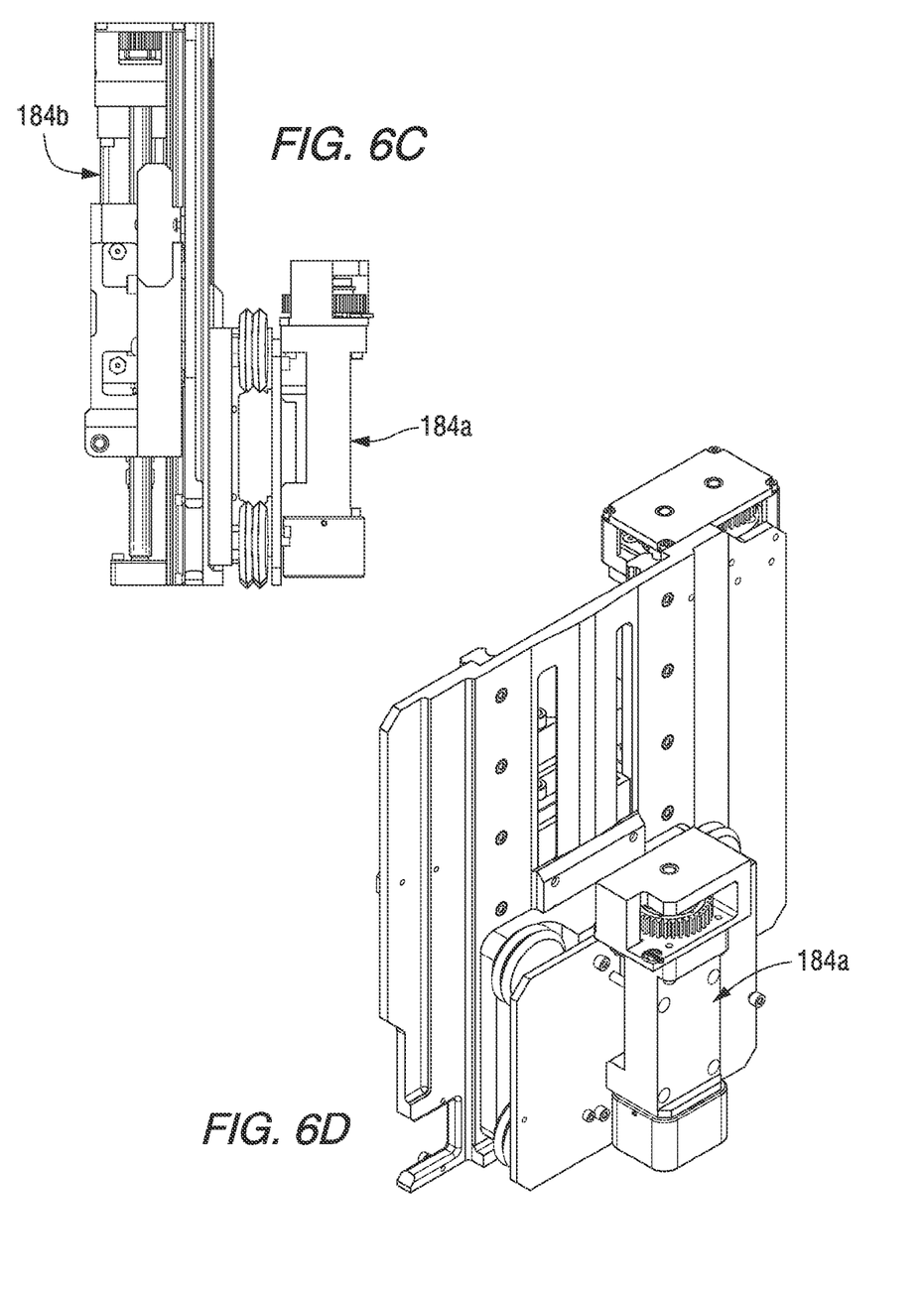

Referring to FIGS. 4 and 5, the frame 112 houses a fixed motor 175 and pinion gear 177 which can be driven and react against a rack gear 178 coupled to the lower track 120. Upon rotation of the frame motor 175, the lower track 120 moves relative to the frame 112.

As shown in FIG. 5 and FIGS. 6A-6D, the lower track 120 houses additional vertical and horizontal precision positioners 180 to provide precision position of tooling sensors or end effectors 182. The carriage system 122 on the lower track 120 houses two motor/gear combinations 184A,B and one pneumatic/hydraulic cylinder 185. One of the motor/gear combinations 184A interfaces with the rack gear 200 coupled to the lower track 120 which allows the carriage system 122 to move along the lower track 120. The other motor/gear combination 184B is coupled to a linear lead screw 190 which drives the pivoting cylinder 185 vertically in the general areas relative to the lower track 120. The pivoting cylinder 185 provides pivoting motion for the attached arm 134 and end effectors 182 for positioning the end effectors 182 away from reactor obstructions. Overall, the apparatus contains seventeen axes of motion to position sensor and end effectors 182 in an efficient method to minimize size, plant shutdown schedule impacts, and personnel radiological exposure, and to maximize end effector coverage on the reactor core shroud around obstructions.

Figure 7:
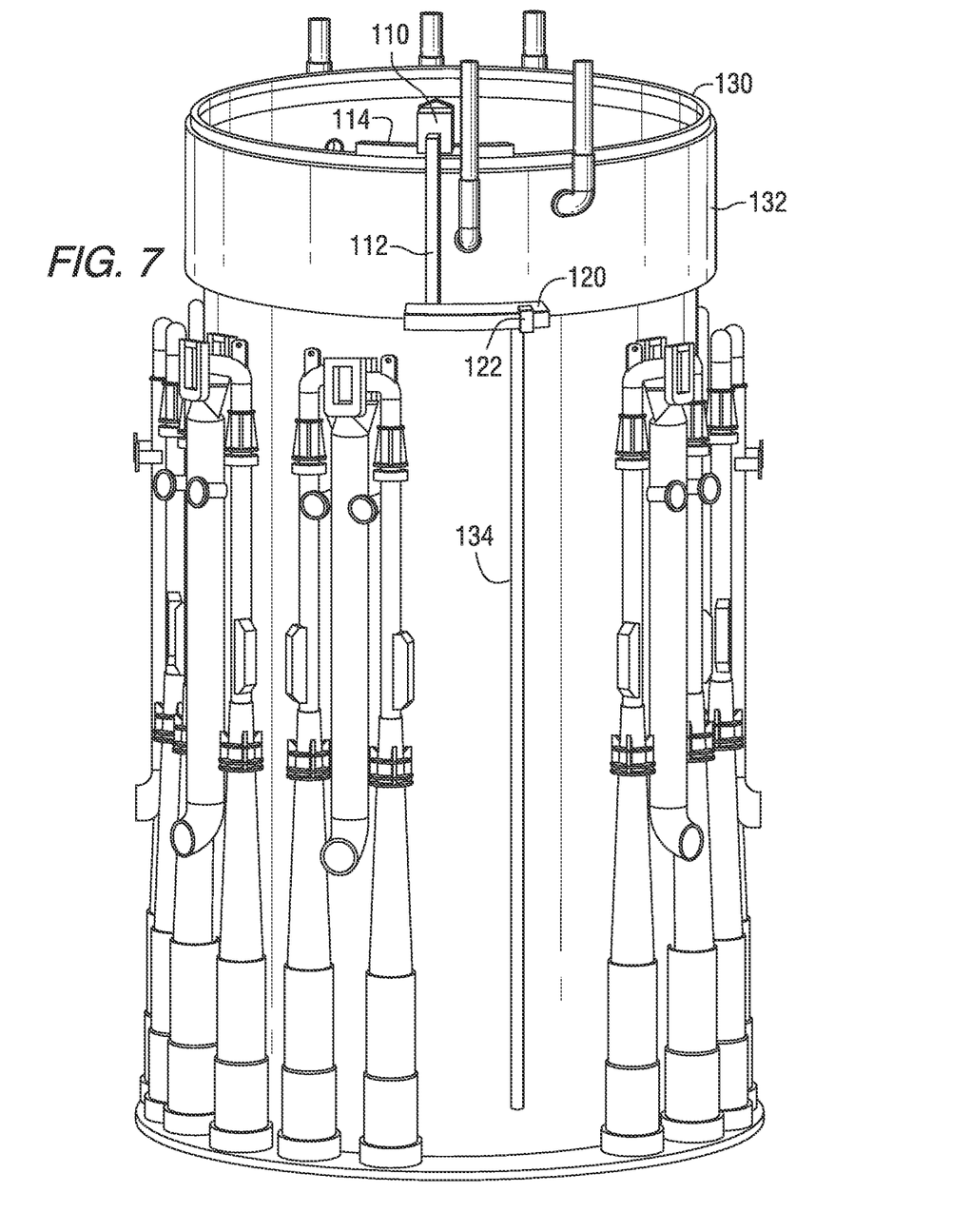
FIG. 7 is a front view of the core shroud inspecting apparatus of FIG. 2 installed on a core shroud of a nuclear reactor with a sensor positioning apparatus attached thereto, in accordance with certain embodiments of the invention.

Referring to FIG. 7, there is illustrated the core shroud inspecting tool 100 (shown in FIG. 2) which is positioned on an annular rim 130 of a core shroud 132. The apparatus 100 extends vertically downward into an annulus space formed between the core shroud 132 and a reactor pressure vessel (not shown). FIG. 7 includes the head 110, frame 112, partial upper track 114, lower track 120, and the carriage 122 (as shown FIG. 2). Further, FIG. 7 includes an arm 134 connected to the carriage 122 and extending vertically downward therefrom along the core shroud 132, and a sensor positioning apparatus 140 in accordance with this invention, connected to the lower end of the arm 134. The arm 134 can further include a sensor (not shown) attached thereto. This sensor and the sensor of the positioning apparatus 140 are capable to detect and analyze the material of the core shroud 132 including any welds contained therein. Suitable sensors for use in this invention can include those devices, such as but not limited to ultrasonic transducers, which are known in the art for inspections. In certain embodiments, multiple sensors can be positioned in a spaced apart relationship to each other along a vertical length of the arm 134. Placement, e.g., spacing, of the sensors can be determined by and correspond to specific areas of the core shroud 132 to be inspected, such as the middle and lower barrels (not shown). In FIG. 7, the lower track 120 is offset from the head 110 and the frame 112, and the carriage 122 with the arm 134 is offset from the lower track 120.

Figure 8A:
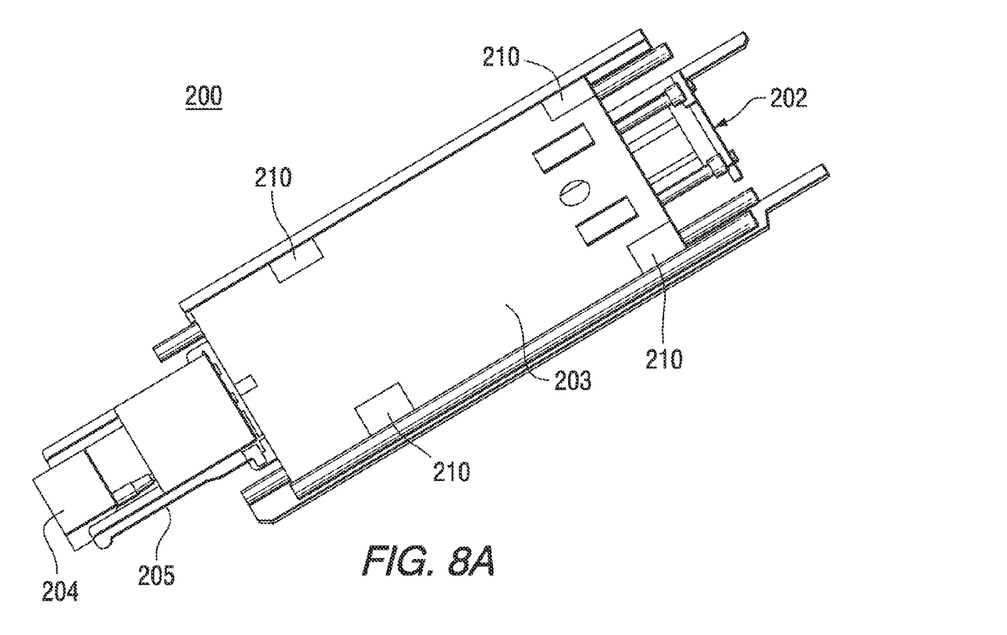
FIG. 8A is a perspective view and 8B is a bottom view of a sensor positioning apparatus, in accordance with certain embodiments of the invention.
Figure 8B:
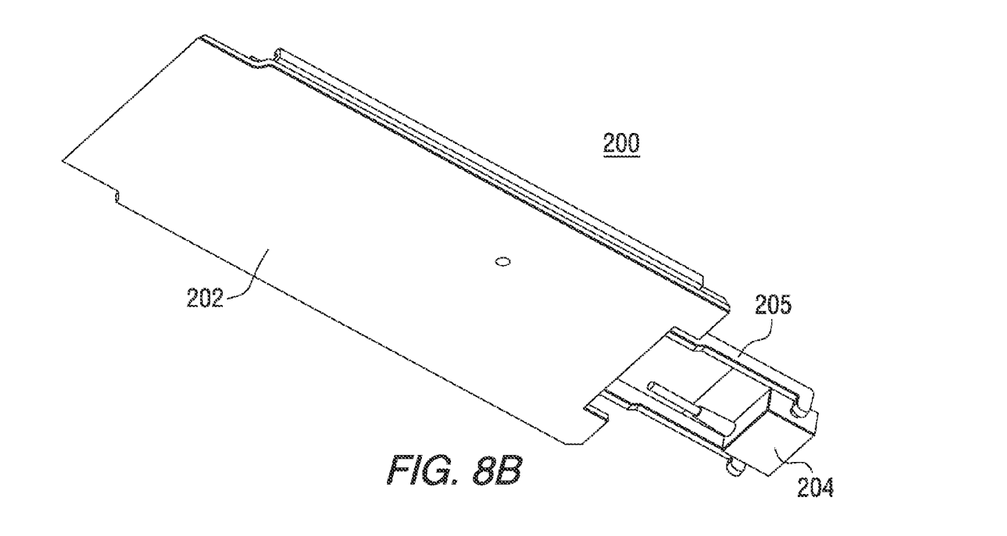

Referring to FIGS. 8A and 8B, there is illustrated a sensor positioning apparatus generally referred to by reference character 200 for controlling the position of a sensor, in accordance with certain embodiments of the invention. FIG. 8A is a perspective view of the apparatus 200 and FIG. 8B is a bottom view of the apparatus 200. As shown in FIG. 8A, the apparatus 200 includes a bottom frame 202 and a top cover 203. The top cover 203 is substantially aligned with and positioned above the bottom frame 202 in a spaced apart relationship such that there is a space or opening formed between the bottom frame 202 and the top cover 203. FIG. 8A also includes a sensor 204 which is connected to the top cover 203 by a gimbal assembly 205 and linear rail support bearings 210 (which are later described). The top cover 203 contains an access hole (not shown) on an end opposite the end to which the sensor 204 is connected, to interface with a manual pick device (not shown). The manual pick device is used to remotely extend or retract the apparatus (e.g., from a component or structure being inspected) in the case of apparatus failure during operation. The bottom frame 202 and the top cover 203 utilize a generally smooth solid finish to prevent snagging on components when locating the sensor positioning apparatus 200 around close proximity obstructions.

Figure 9:
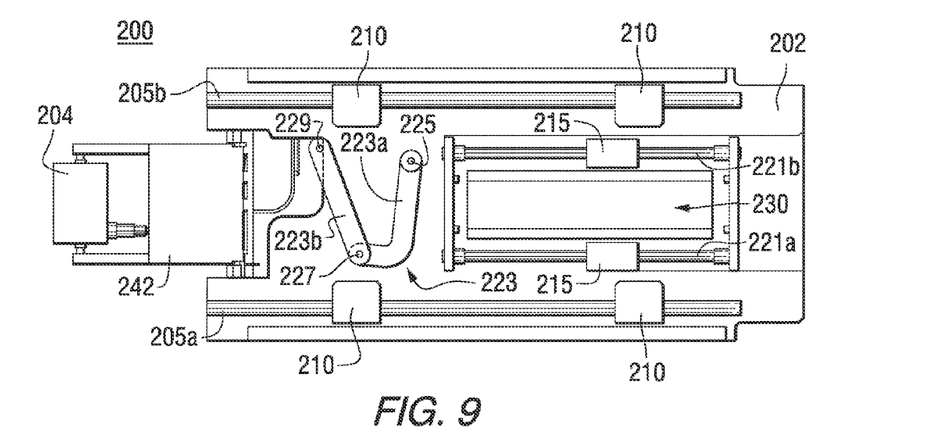
FIG. 9 is a top view of the sensor positioning apparatus of FIG. 8A with the top cover removed, in accordance with certain embodiments of the invention.

Referring to FIG. 9, there is illustrated the apparatus 200 as shown in FIGS. 8A and 8B. FIG. 9 is a top view of the apparatus 200 with the top cover 203 (as shown in FIG. 8A) removed. FIG. 9 includes the bottom frame 202 and the sensor 204 as shown in FIGS. 8A and 8B. FIG. 9 also includes a first linear rail 205*a* and a second linear rail 205*b* positioned parallel to each other, and fixedly attached to the bottom frame 202. Linear rail support bearings 210 are horizontally movably connected to each of the first and second linear rails 205*a,b*, in a spaced apart relationship. Each of the linear rail support bearings 210 positioned on the first linear rail 205*a* are substantially aligned parallel to each of the linear rail support bearings 210 positioned on the second linear rail 205*b*. Each of the linear rail support bearings 210 are coupled to the top cover 203 (as shown in FIG. 8A) such that when the top cover 203 is moved horizontally, the linear rail support bearings 210 travel in a corresponding horizontal direction along the first and second linear rails 205*a,b*. FIG. 9 shows two linear rail support bearings 210 on each of the first and second linear rails 205*a,b*. However, it is understood that one or more linear rail support bearings may be used. Since the sensor 204 is connected to the top cover 203 (as shown in FIG. 8A), the linear rail support bearings 210 are also operable to guide the sensor 204 from a first position, e.g., closed position, to a second position, e.g., extended position (shown in phantom lines in FIG. 9).

FIG. 9 also shows a rodless cylinder carriage 215 which includes two custom-machined hydraulic cylinders 221*a,b*. A portion of these cylinders 221*a,b* are attached to the top cover 203 (as shown in FIG. 8A) and operable to drive the top cover 203 and the sensor 204 from a closed position to an extended position. In certain embodiments, the hydraulic cylinders 221a,b employed are sealed rodless cylinders with magnetically coupled cylinder carriages. Without intending to be bound by any particular theory, it is believed that the use of these cylinders provide at least one of the following three design advantages over conventional cylinders known in the art: (i) a slim profile for maximum access in limited access areas, (ii) magnetic coupling to provide fail safe operation during unplanned collisions (e.g., the cylinders will decouple upon contact with an obstruction), and (iii) sealed enclosure to eliminate dynamic sealing and associated reliability concerns with under water usage. The apparatus 200 can be controlled with hydraulic pumps and valves to move a precise amount of hydraulic fluid into the cylinders 221a,b which will lock the cylinders in position. In contrast to pneumatic clylinders, the use of hydraulics allows the apparatus 200 to position the sensor 207 in any fixed position from a closed to a fully extended position.

Further, shown in FIG. 9 is a two bar linkage 223 having a first bar 223a and a second bar 223b. One end of the first bar 223a is connected to a first pin 225 which is attached to the bottom frame 202. The other end of the first bar 223a is connected to a pivot pin 227. One end of the second bar 223b is connected to a second pin 229 which is attached to the upper cover 203. The other end of the second bar 223b is connected to the pivot pin 227.

Figure 10A:
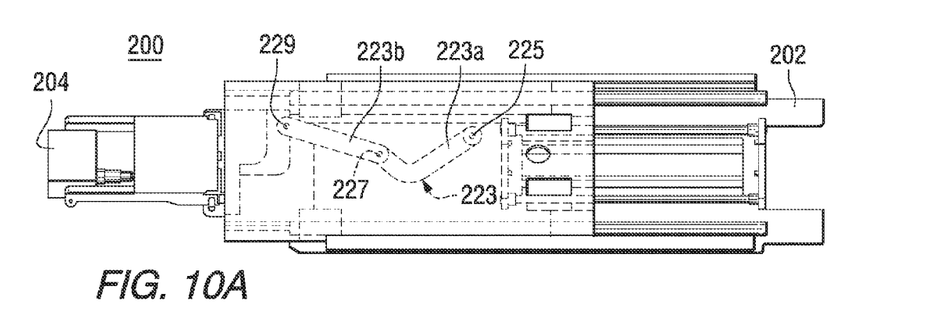
Figure 10B:
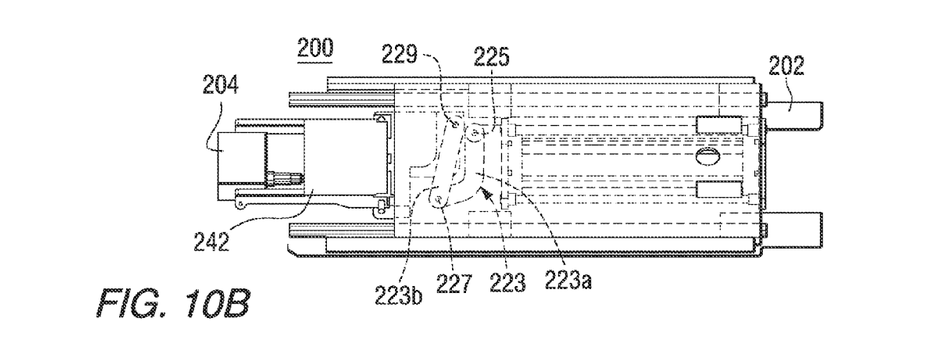

Referring to FIGS. 10A and 10B, there is illustrated the apparatus 200 as shown in FIG. 9. FIGS. 10A and 10B include the bottom frame 202, sensor 204, two bar linkage 223, first bar 223a, second bar 223b, first pin 225, pivot pin 227 and second pin 229. FIG. 10A shows the two bar linkage 223 in an extended configuration when the sensor 204 is in an extended position. FIG. 10B shows the two bar linkage 223 in a compressed configuration when the sensor 204 is in a closed position.

Referring to FIG. 9, a cable protective covering 230 is connected to the bottom frame 202 to provide protection of cables and/or tubing (not shown) from getting pinched in moving parts or plant obstructions. In certain embodiments, the cable is utilized for sensor signal and power passage. For example, cable (not shown) can be connected to the sensor 204 and extend underneath the protective plate 242 through the first and second bars 223a,b of the two bar linkage 223 and underneath the protective covering 230. The cable (not shown) can be connected to the first and second bars 223a,b such that it is extended or contracted as the two bar linkage 223 extends and contracts in accordance with horizontal movement of the top cover 203 (as previously discussed herein and shown in FIGS. 10A and 10B). Thus, the two bar linkage 223 can serve the purpose of cable management to prevent extremely sensitive cable from getting pinched and provides a mechanism to maintain minimum bend radius of the cabling during actuation of the apparatus 200.

In certain embodiments, the apparatus of the invention can be utilized to position a sensor relative to another sensor that is attached to an inspection tool. For example, for illustrative purposes, a sensor is at a fixed elevation on an inspection tool arm, e.g., 60 inches, the tool has 10 inches of stroke, there is one sensor attached to the middle of the arm and one sensor attached to the end of the arm. Thus, this setup can scan a weld from 30 to 40 inches and from 60 to 70 inches. Thus, if there are welds to be examined at 32 and 62 inches, for example, this setup is capable of performing the weld exams in parallel. However, if the welds were located at 32 and 63 inches, the weld examinations would have to be performed separately because the sensors are not in the exact same location relative to each weld. In this scenario, the inspection tool in combination with the apparatus of the invention can perform both examinations within the same tool setup. For example, a scan of 32 to 34 inches (i.e., 2 inch stroke is required for examination), then 63 to 65 inches can be performed. Installation of the apparatus of the invention on the inspection tool allows the separation between the sensors to be set to exactly 31 inches and the inspections could be performed at the same time. In an alternative setup, if the welds were at 38 and 70 inches, the inspection tool without the apparatus of the invention would have to be reconfigured to perform the examination, while the tool with this apparatus of the invention can perform the examinations at the same time without any tool reconfigurations.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

We claim:

1. A robotic apparatus for remotely positioning a sensor in a nuclear reactor, comprising:
   a sensor;
   a bottom frame;
   a top cover having a first end and an opposite second end, the sensor connected to the first end, the top cover positioned parallel to the bottom frame and spaced apart from the bottom frame;
   a first linear rail connected to the bottom frame;
   a second linear rail connected to the bottom frame, substantially aligned in a parallel relationship to the first linear rail and spaced apart from the first linear rail;
   a first linear rail support coupled to the top cover and movably connected to the first linear rail;
   a second linear rail support coupled to the top cover and movably connected to the second linear rail; and
   a plurality of hydraulic cylinders attached to the top cover and structured to drive and move the top cover a distance in a horizontal direction, thereby moving the sensor connected to the top cover an equivalent distance in the horizontal direction, relative to the bottom frame, and thereby moving in a horizontal direction the first and second linear rail supports, coupled to the top cover, relative to the first and second linear rails, respectively.

2. The apparatus of claim 1, further comprising a two bar linkage system, the linkage system comprising:
   a first bar having a first end and a second end;
   a second bar having a first end and a second end;
   the first end of the first bar connected to a first pin which is attached to the bottom frame;
   the second end of the first bar connected to a pivot pin;
   the first end of the second bar connected to a second pin which is attached to the top cover; and
   the second end of the second bar connected to the pivot pin,
   wherein when the top cover is moved horizontally the two bar linkage system is in an extended position.

3. The apparatus of claim 1, wherein the plurality of hydraulic cylinders comprises two hydraulic cylinders.

4. A system for inspection in a nuclear reactor, which comprises:
- a reactor pressure vessel having a wall;
- a core shroud having an annular rim;
- an annulus formed between the core shroud and the wall of the reactor pressure vessel;
- an inspection tool connected to the core shroud and positioned in the annulus, which comprises:
  - an upper portion of the inspection tool positioned on the annular rim of the core shroud;
  - an arm of the inspection tool coupled to the upper portion and extending vertically downward along the core shroud in the annulus; and
- a robotic apparatus connected to the arm of the inspection tool, the robotic apparatus, which comprises:
  - a sensor;
  - a bottom frame;
  - a top cover having a first end and an opposite second end, the sensor connected to the first end, the top cover positioned parallel to the bottom frame and spaced apart from the bottom frame;
  - a first linear rail connected to the bottom frame;
  - a second linear rail connected to the bottom frame, substantially aligned in a parallel relationship to the first linear rail and spaced apart from the first linear rail;
  - a first linear rail support coupled to the top cover and movably connected to the first linear rail;
  - a second linear rail support coupled to the top cover and movably connected to the second linear rail; and
  - a plurality of hydraulic cylinders attached to the top cover and structured to drive and move the top cover a distance in a horizontal direction, thereby moving the sensor connected to the top cover an equivalent distance in the horizontal direction, relative to the bottom frame, and thereby moving in a horizontal direction the first and second linear rail supports, coupled to the top cover, relative to the first and second linear rails, respectively,
wherein, the sensor is effective to inspect a component in a nuclear reactor.

5. The system of claim 4, wherein the upper portion comprises a partial upper track positioned on the annular rim of the core shroud and horizontally movable along the rim.

6. The system of claim 5, wherein the inspection tool further comprises:
- an assembly, which comprises:
  - a head movably connected to the partial upper track such that the head is horizontally movable along the partial upper track;
  - a lower track;
  - a frame having a first end and a second end, the first end being mounted to the head and the second end being connected to the lower track such that the lower track is horizontally movable along the core shroud;
  - a carriage movably connected to the lower track and having one end of the arm connected thereto and the other opposite end of the arm having connecting thereto the robotic apparatus, and extending vertically downward along the core shroud;
  - a first driving mechanism connected to the head and the partial upper track, and structured to drive the head along the partial upper track and to drive the partial upper track along the rim;
  - a second driving mechanism connected to the frame and structured to drive the lower track along the core shroud; and
  - a third driving mechanism connected to the carriage and structured to drive said carriage along the lower track; and
- a track brake system connected to the partial upper track,
  - wherein, when the track brake system is activated, the partial upper track remains stationary and the head is movable along the partial upper track, and
  - wherein, when the track brake system is deactivated, the partial upper track can be driven into a different position along the annular rim of the core shroud.

7. The system of claim 6, wherein bearing wheels are attached to the frame such that the frame is horizontally movable along the lower track.

* * * * *